(12) United States Patent
Imaoka et al.

(10) Patent No.: US 7,210,782 B2
(45) Date of Patent: May 1, 2007

(54) EYE IMAGING DEVICE

(75) Inventors: Takuya Imaoka, Yokohama (JP); Jyoji Wada, Yokohama (JP); Toshiaki Sasaki, Chofu (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 438 days.

(21) Appl. No.: 10/509,349

(22) PCT Filed: Mar. 25, 2003

(86) PCT No.: PCT/JP03/03634

§ 371 (c)(1),
(2), (4) Date: Sep. 28, 2004

(87) PCT Pub. No.: WO03/082114

PCT Pub. Date: Oct. 9, 2003

(65) Prior Publication Data

US 2005/0117782 A1 Jun. 2, 2005

(30) Foreign Application Priority Data

Mar. 29, 2002 (JP) ............................. 2002-096057

(51) Int. Cl.
*A61B 3/14* (2006.01)
(52) U.S. Cl. ..................................... 351/206
(58) Field of Classification Search ................ 351/206, 351/205, 207, 211, 212, 221
See application file for complete search history.

(56) References Cited

U.S. PATENT DOCUMENTS 4,770,523 A * 9/1988 Yamada ...................... 351/212
6,758,564 B2 * 7/2004 Ferguson .................... 351/221

FOREIGN PATENT DOCUMENTS

| JP | 62-90133 | 4/1987 |
|----|----------|--------|
| JP | 11-47117 | 2/1999 |
| JP | 2001-17410 | 1/2001 |

* cited by examiner

*Primary Examiner*—Ricky Mack
*Assistant Examiner*—Tuyen Tra
(74) *Attorney, Agent, or Firm*—Pearne & Gordon LLP

(57) ABSTRACT

The present invention aims to expand a range through which a guiding visible light for guiding a position of an eye appears in shooting an image of the eye and to put easily the position of the eye onto an optical axis of an imaging optical system in shooting.

In the present invention, an eye image pick-up system (10) includes a lens (13), a lens-barrel (12) for supporting the lens (13), a mirror (14) as a guiding mirror for turning an optical path of an imaging optical system at an almost right angle and guiding a guiding visible light, an imaging device (16) for picking up an image of an eye (11), and an LED (15) provide at the back of the mirror (14) on a prolonged line of an optical axis (17) extending from the lens (13) to the mirror (14) to emit the guiding visible light. The mirror (14) has a reflecting film (18) formed by depositing reflecting material onto a transparent substrate, and a circular-ring light guiding portion (19) made of transparent material. The guiding visible light from the LED (15) is guided to pass through the light guiding portion (19) and arrives at the eye (11) via the lens (13). Full circular-ring guiding visible lights are viewed when the position of the eye (11) is put onto the optical axis (17), and the circular-ring guiding visible lights a part of which is lost are viewed when the position of the eye (11) is out of the optical axis (17).

14 Claims, 8 Drawing Sheets

FIG. 12

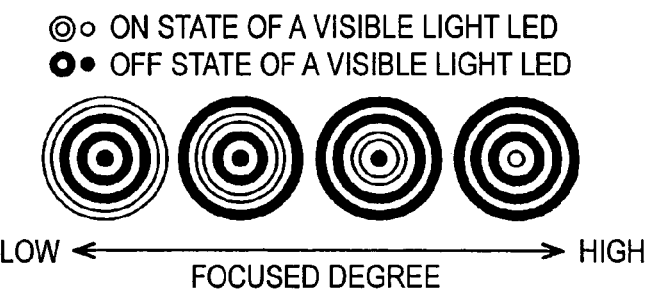

◎○ ON STATE OF A VISIBLE LIGHT LED
○● OFF STATE OF A VISIBLE LIGHT LED

LOW ←――― FOCUSED DEGREE ―――→ HIGH

FIG. 13

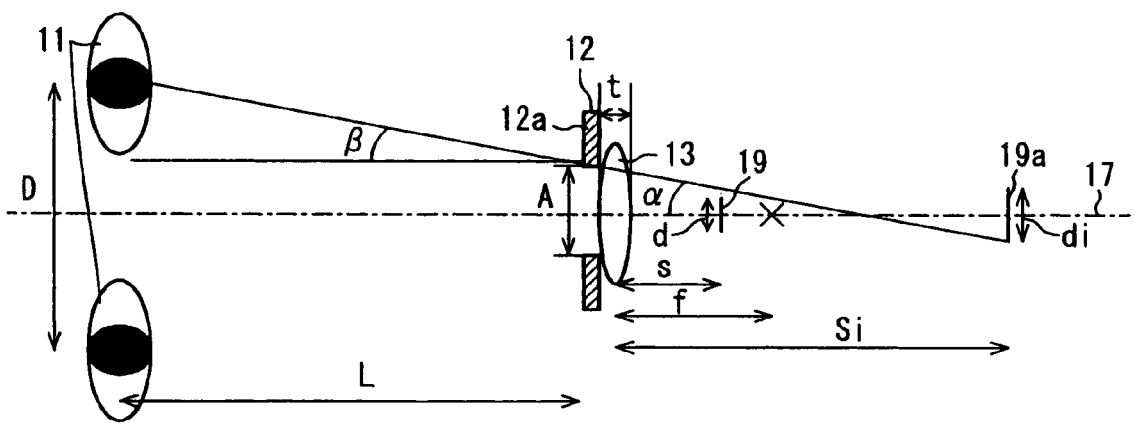

A: APERTURE DIAMETER OF THE LENS-BARREL
t: THICKNESS OF THE LENS
s: DISTANCE BETWEEN THE LENS AND THE LIGHT GUIDING PORTION
si: DISTANCE BETWEEN THE LENS AND AN IMAGE ON THE LIGHT GUIDING PORTION
f: FOCAL LENGTH OF THE LENS
d: DIAMETER (SIZE) OF THE LIGHT GUIDING PORTION
di: DIAMETER (SIZE) OF AN IMAGE ON THE LIGHT GUIDING PORTION
L: SUBJECT DISTANCE IN THE EYE IMAGE PICK-UP SYSTEM
D: INTERVAL BETWEEN BOTH EYES

EYE IMAGING DEVICE

TECHNICAL FIELD

The present invention relates to an eye image pick-up system that picks up an image of an eye of a human being to identify the individual by its feature.

BACKGROUND ART

In the personal authentication in the access management or the automatic settling system, the identification of the user in using the computer or the mobile phone, and so forth, an iris image obtained by shooting the eye is utilized. In order to put exactly a position of the eye to be shot onto an optical axis of an imaging optical system, the eye image pick-up system for shooting the eye utilizes the eye position guiding device.

For instance, in the eye image pick-up system in Patent Application No. 2000-367389 filed previously by the applicant of this application, as shown in FIG. 15(a), the eye position guiding device including a lens-barrel 112 provided concentrically with the optical axis of the imaging optical system, an objective lens 113, a mirror 114 for changing an optical path of the imaging optical system, an LED 115 arranged at the back of the mirror 114 on a prolonged line of the optical axis to emit a visible light, and an imaging device 116 for picking up the image of the eye is provided.

As shown in FIG. 15(b), the mirror 114 has a reflecting surface 118 formed of a deposited film, or the like made of reflecting material, and a transparent light guiding portion 119 provided concentrically with the optical axis and not deposited. As shown in FIG. 15(c), in the case where the eye to be shot is put onto the optical axis, a light of the LED 115 passed through the light guiding portion 119 appears as a guiding visible light in the lens-barrel 112 when the user views from a front edge of the lens-barrel 112. In contrast, in the case where the eye is displaced from the optical axis, the light of the LED 115 does not appear in the lens-barrel 112. Therefore, when the user as a subject moves his or her eye to find the light of the LED 115, the user's eye is guided onto the optical axis.

However, in the above eye position guiding device, a range within which the user can look at the light of the LED 115 via the lens-barrel 112 is narrow. Therefore, it is difficult for the user to find the light of the LED and thus in some cases it takes a lot of time to put the position of the eye onto the optical path.

Also, it is hard to decide whether or not the image of the eye to be shot is focused properly, and thus it is sometimes hard to decide in which direction the position of the eye should be moved back and forth to focus. In addition, it is sometimes hard to discriminate with which eye of left and right eyes the user looks at the LED.

Also, the light guiding portion is formed by removing the deposited portion from a mirror, which is formed by depositing aluminum on a transparent substrate such as a glass plate, or the like, by means of the etching process. Therefore, the steps become complicated and thus in some cases a production cost is increased.

DISCLOSURE OF THE INVENTION

The present invention has been made in view of the above circumstances, and it is an object of the present invention to provide an eye image pick-up system that has an eye position guiding device for guiding an position of an eye to be shot when a user looks at a visible-light light source provided onto an optical axis of an imaging optical system through a light guiding means, and also permits the user as a subject to find easily out a guiding visible light and guide quickly the position of the eye onto an optical axis.

An eye image pick-up system of the present invention for picking up an image of an eye by using an objective lens and an imaging device, comprises a mirror portion provided between the objective lens and the imaging device, for turning an optical path of an optical system;

a light source provided at a back of the mirror portion on a prolonged line of the optical axis that extends from the objective lens to the mirror portion in the optical path, for emitting a visible light; and a light guiding means provided to the mirror portion, for guiding the visible light from the light source to an objective lens side; wherein the light guiding means is constructed by translucent members that are provided concentrically round the optical axis.

According to the above configuration, the user can find easily the guiding visible light via the light guiding means provided concentrically with the optical axis of the eye image pick-up system, and also can discriminate easily whether or not the user's own eye is put on the optical axis. Therefore, the user can guide easily the position of the eye onto the optical axis.

Also, in the eye image pick-up system of the present invention, the light guiding means has a circular-ring translucent portion formed round the optical axis on a reflecting surface of the mirror portion.

According to the above configuration, the user can find easily the guiding visible light by the light guiding means that are arranged like the circular ring. Therefore, the user can guide simply the position of the eye onto the optical axis of the eye image pick-up system.

Also, in the eye image pick-up system of the present invention, the light guiding means has a plurality of translucent portions formed on a reflecting surface of the mirror portion and arranged on a circle round the optical axis.

According to the above configuration, the user can guide simply the position of the eye onto the optical axis by the light guiding formed of a plurality of translucent portions that are arranged on a circle like the circular ring. Also, in this case, since an area of the light guiding means on the reflecting surface of the mirror portion is relatively small, a loss of a quantity of light that comes up to the imaging device can be reduced.

Also, in the eye image pick-up system of the present invention, the plurality of translucent portions of the light guiding means are formed of a plurality of triangular translucent portions that are aligned at an equal angle on a circle round the optical axis to direct respective sharp angles to the optical axis.

According to the above configuration, the user can recognize simply the direction of the optical axis based on the direction of the apex of the triangle. Therefore, the user can guide quickly the position of the eye onto the optical axis.

Also, in the eye image pick-up system of the present invention, the plurality of translucent portions of the light guiding means are formed of a plurality of arrow-shaped translucent portions that are aligned at an equal angle on a circle round the optical axis to direct respective pointed portions to the optical axis.

According to the above configuration, the user can recognize simply the direction of the optical axis based on the direction of the arrow. Therefore, the user can guide quickly the position of the eye onto the optical axis.

Also, in the eye image pick-up system of the present invention, the light guiding means has a plurality of circular-ring or circular translucent portions that are formed concentrically round the optical axis on a reflecting surface of the mirror portion, and the light source has a plurality of light sources at least adjacent light sources of which emit lights in different colors to the plurality of translucent portions.

According to the above configuration, the user can know a displacement of the position of the eye or the direction displaced from the optical axis by change in the color of the light source viewed via the light guiding means. Therefore, even the weak-sighted person can guide easily the position of the eye onto the optical axis.

Also, in the eye image pick-up system of the present invention, the light guiding means has a plurality of circular-ring or circular translucent portions that are formed concentrically round the optical axis on a reflecting surface of the mirror portion, the translucent portions are formed of colored translucent portions at least adjacent translucent portions of which pass through lights in different colors, and the light source has a white light source that emits a light to the plurality of translucent portions.

According to the above configuration, the user can know a displacement of the position of the eye or the direction displaced from the optical axis by change in the color of the light source viewed via the light guiding means. Also, in this case, since the light source is composed of the white light source, the eye image pick-up system can be constructed at a low cost.

Also, in the eye image pick-up system of the present invention, the light guiding means has translucent portions formed of openings that are formed on a reflecting surface of the mirror portion.

According to the above configuration, the light guiding means can be implemented with a simple configuration.

Also, in the eye image pick-up system of the present invention, the mirror portion is molded with resin material on one surface of which a reflecting surface is formed, and the light guiding means has a plurality of translucent portions formed of openings that are aligned on a circle round the optical axis on a reflecting surface of the mirror portion.

According to the above configuration, the mirror portion having the light guiding means can be formed by the integral molding of the resin. Therefore, the eye image pick-up system can be constructed at a low cost.

Also, in the eye image pick-up system of the present invention, the mirror portion has a holding portion that is provided to communicate with the openings and holds the light source.

According to the above configuration, the mirror portion including the light guiding means and the light source can be constructed integrally. Therefore, the number of articles can be reduced because the holding member is not required separately, and the assembling can be facilitated. As a result, reduction in size and cost of the eye image pick-up system can be achieved.

Also, in the eye image pick-up system of the present invention, the light source has a plurality of color light sources that emit a light in different colors respectively, and the eye image pick-up system further comprises a focusing deciding means for deciding a focused condition of the image of the eye picked up by the imaging device; and a light emission controlling means for controlling light emitting times of the light sources in respective colors based on a decision result of the focused condition.

According to the above configuration, the user can recognize the focused condition based on the colors of the visible lights from the light sources. Therefore, the user can guide easily the position of the eye to the focusing point.

Also, the eye image pick-up system of the present invention further comprises a focusing deciding means for deciding a focused condition of the image of the eye picked up by the imaging device; and a light emission controlling means for changing a number of lights that pass through the plurality of translucent portions of the light guiding means, in response to a decision result of the focused condition.

According to the above configuration, the user can recognize the focused condition based on the number of lights emitted from the light source through the translucent portions. Therefore, the user can guide easily the position of the eye to the focusing point.

Also, the eye image pick-up system of the present invention further comprises a focusing deciding means for deciding a focused condition of the image of the eye picked up by the imaging device; and a light emission controlling means for changing positions of lights that pass through the plurality of translucent portions of the light guiding means, in response to a decision result of the focused condition.

According to the above configuration, the user can recognize the focused condition based on the positions of lights emitted from the light source through the translucent portions. Therefore, the user can guide easily the position of the eye to the focusing point.

Also, in the eye image pick-up system of the present invention, the light source the light source has a plurality of color light sources that emit a light in different colors respectively, and the eye image pick-up system further comprises an image discriminating means for discriminating to which one of right and left eyes the eye the image of which is picked up by the by the imaging device corresponds; and a light emission controlling means for changing a color of a light emitted from the light source in response to a decision result of the focused condition.

According to the above configuration, the user can know easily which eye of right and left eyes corresponds to the eye that is now to be picked up, based on the color of the visible light from the light source. Therefore, the user can guide quickly the position of the eye onto the optical axis.

BRIEF DESCRIPTION OF THE DRAWINGS

FIGS. 1(a) and 1(b) are views showing a configuration of an eye image pick-up system according to a first embodiment of the present invention, wherein FIG. 1(a) is an explanatory view showing a basic configuration of the eye image pick-up system, and FIG. 1(b) is a plan view showing a structure of a mirror.

FIGS. 2(a) to 2(f) are views showing an eye position guiding action in the eye image pick-up system according to the first embodiment of the present invention, wherein FIGS. 2(a) and 2(d) show a positional relationship between an optical axis and an eye in the eye image pick-up system respectively, FIGS. 2(b) and 2(e) show an appearance of a guiding visible light respectively, and FIGS. 2(c) and 2(f) show an example of an image picked up by the imaging device respectively, and FIGS. 2(a), 2(b), and 2(c) show respectively the case where the position of the eye is put onto the optical axis and FIGS. 2(d), 2(e), 2(f) show respectively the case where the position of the eye is displaced from the optical axis.

FIG. 12 is a plan view showing a configuration of an LED portion in a second variation according to the fourth embodiment of the present invention.

FIG. 13 is an explanatory view showing an arrangement of constituent elements of an eye image pick-up system according to a fifth embodiment of the present invention.

FIGS. 15(a) to 15(c) are views showing an eye image pick-up system in the prior art, wherein FIG. 15(a) is an explanatory view showing a basic configuration, FIG. 15(b) is a plan view showing a structure of a mirror, and FIG. 15(c) is an explanatory view showing an appearance of a guiding visible light.

Figure 1:
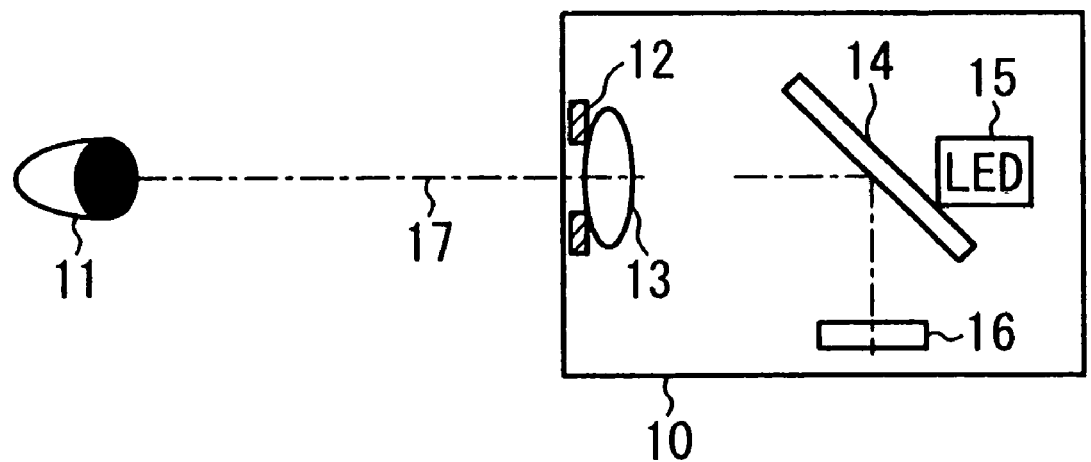
Figure 1:
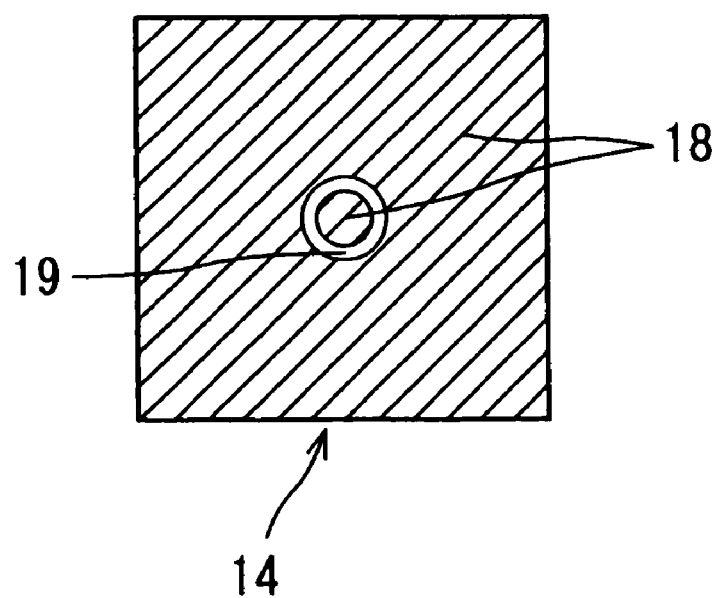

In the drawings, a reference numeral 10 refers to an eye image pick-up system; 11 to an eye; 12 to a lens-barrel; 12a to a front edge of the lens-barrel; 13 to lens; 14, 20, 30, 40, 50, 60, 70 and 80 to a mirror; 15, 96, 97, 104 and 105 to a LED; 16 to an imaging device; 17 to an optical axis; 18, 21, 31, 41, 51, 61, 71 and 81 to reflecting film; 19, 22, 32, 42, 52, 62, 72 and 82 to a light guiding portion; 83 LED holding portion; 90 and 100 to a LED portion; 91 to a signal processing portion; 92 to a focusing deciding portion; 93 and 102 to a control portion; 94 to a switch A; 95 to a switch B; 101 to an image recognition processing portion; and 103 to a switch.

BEST MODE FOR CARRYING OUT THE INVENTION

Embodiments of the present invention will be explained with reference to the drawings hereinafter.

(First Embodiment)

FIGS. 1(a) and 1(b) are views showing a configuration of an eye image pick-up system according to a first embodiment of the present invention, wherein FIG. 1(a) is an explanatory view showing a basic configuration of the eye image pick-up system, and FIG. 1(b) is a plan view showing a structure of a mirror.

As shown in FIG. 1(a), an eye image pick-up system 10 according to the present embodiment is a camera that gets an image of an iris, or the like by shooting an eye 11, and is constructed to include a lens 13, a lens-barrel 12 for supporting the lens 13, a mirror 14 as a guiding mirror in which a reflecting film is provided at an inclination of about 45 degree to turn an optical path of the imaging optical system at an almost right angle, and an imaging device 16 for picking up the image of the eye 11, which is focused by the lens 13, by means of the photoelectric conversion.

Also, a light emitting diode (abbreviated as an "LED" hereinafter) 15 as a light source to emit a guiding visible light is provided at the back of the mirror 14 on a prolonged line of an optical axis 17 that extends from the eye 11 to the mirror 14 to pass through a center of the lens 13.

As shown in FIG. 1(b), the mirror 14 comprises a reflecting film 18 in which a reflecting surface is formed by depositing selectively an aluminum on a transparent substrate made of a plate-like glass or resin, and a light guiding portion 19 as a transparent translucent portion that is formed like a circular ring and not deposited with the aluminum. A center of a circle of the light guiding portion 19 is arranged to coincide with the optical axis 17 in the eye image pick-up system 10. Thus, the visible light emitted from the LED 15 transmits through the light guiding portion 19 and comes up to the eye 11 via the lens 13.

Figure 2:
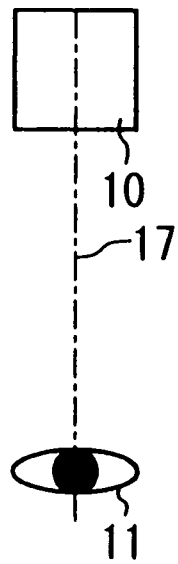
Figure 2:
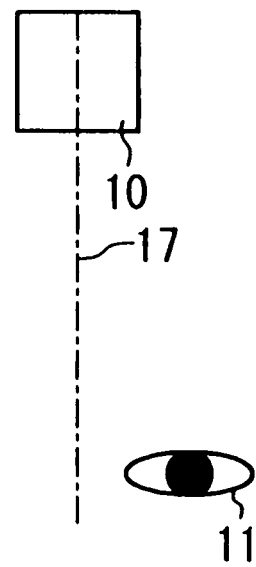
Figure 2:
Figure 2:
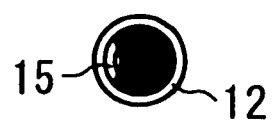
Figure 2:
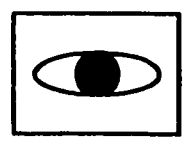
Figure 2:
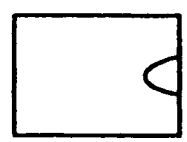

Next, an eye position guiding action in the eye image pick-up system 10 according to the first embodiment constructed as above will be explained with reference to FIG. 2 hereunder. In FIGS. 2(a) to 2(f), FIGS. 2(a) and 2(d) show a positional relationship between the optical axis and the eye in the eye image pick-up system respectively, FIGS. 2(b) and 2(e) show an appearance of the guiding visible light respectively, and FIGS. 2(c) and 2(f) show an example of the image picked up by the imaging device respectively, and also FIGS. 2(a), 2(b), and 2(c) show respectively the case where the position of the eye is put onto the optical axis and FIGS. 2(d), 2(e), and 2(f) show respectively the case where the position of the eye is displaced from the optical axis.

In the eye image pick-up system 10 according to the present embodiment shown in FIG. 1(a), when the eye 11 is put onto the optical axis 17 as shown in FIG. 2(a), the circular-ring visible light being emitted from the LED 15 and guided to pass through the light guiding portion 19 looks like the concentric visible light in the lens-barrel 12 as shown in FIG. 2(b) when the user as the subject views a front edge of the lens-barrel 12. At this time, the image picked up by the imaging device 16 looks like such an image that the eye is positioned at the center as shown in FIG. 2(c).

In contrast, when the position of the eye 11 is displaced from the optical axis 17 as shown in FIG. 2(d), the visible light emitted from the LED 15 and guided via the light guiding portion 19 looks like a circular ring a part of which is notched as shown in FIG. 2(e). At that time, the picked-up image looks like such an image that the eye is out of center as shown in FIG. 2(f).

As a result, according to the eye image pick-up system in the first embodiment, since the guiding visible light from the LED 15 is shaped into the circular ring, such visible light is found within a wide range on the subject side, and thus the eye position guiding device that makes it possible for the user to find easily the guiding visible light can be implemented. Also, in this case, according to the position where the circular ring of the guiding visible light is lost, it is possible for the user to recognize simply the direction toward which the position of the eye should be moved. Therefore, the position of the eye can be guided quickly onto the optical axis 17 and also the position of the eye can be moved quickly up to the position that is suitable for the shooting.

Next, several variations of the configuration of the light guiding portion of the mirror will be explained with reference to the drawings hereunder.

Figure 3:
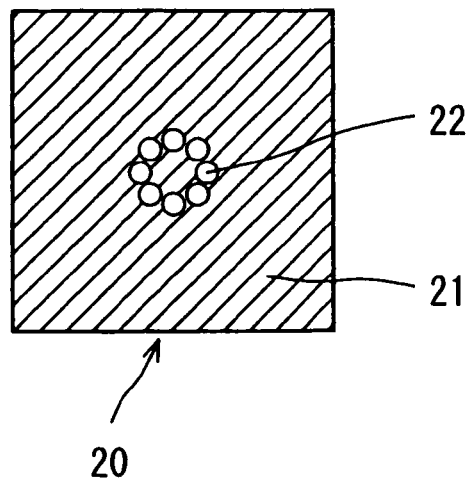
FIG. 3 is a plan view showing a structure of a mirror in a first variation according to the first embodiment of the present invention.

FIG. 3 is a plan view showing a structure of a mirror in a first variation according to the first embodiment of the present invention. In this first variation, the shape of the light guiding portion in the first embodiment is varied to arrange a plurality of translucent portions like a circular ring. Like the first embodiment shown in FIG. 1(b), a mirror 20 in the first variation is constructed to have a reflecting film 21 formed by depositing aluminum on the transparent substrate, and a transparent light guiding portion 22 that has no deposition thereon. The light guiding portion 22 comprises a plurality (eight in FIG. 3) of circular translucent portions that are arranged at an equal interval (equal angle) on a circle round the optical axis.

According to this structure, when the position of the eye is put on the optical axis, the user can see the guiding visible light from the LED 15 through all of a plurality of circular translucent portions constituting the light guiding portion 22. That is, the user can see the circular guiding visible lights aligned like the circular ring in the lens-barrel 12. Also, when the position of the eye is displaced from the optical axis, some of the circular guiding visible lights aligned like the circular ring disappear. That is, the guiding visible light looks like the circular-ring guiding visible lights a part of which is lost.

Therefore, since the user can understand immediately the direction toward which the position of the eye should be moved, based on the lost position in the guiding visible light when the position of the eye must be moved, the user can move quickly the position of the eye. Also, since an area of the reflecting film 21 becomes wide relatively in contrast to the structure in FIG. 1, a loss of a quantity of light of the picked-up image in the mirror 20 can be reduced. In this case, eight circular translucent portions constituting the light guiding portion 22 are illustrated in FIG. 3, but the number of the translucent portions is not limited to this and any number in excess of 2 may be employed. In the case where the number of the translucent portions arranged in the mirror 20 is reduced, such an arrangement may be employed that, for example, a plurality of translucent portions are positioned in the direction toward which the position of the eye is often displaced.

Figure 4:
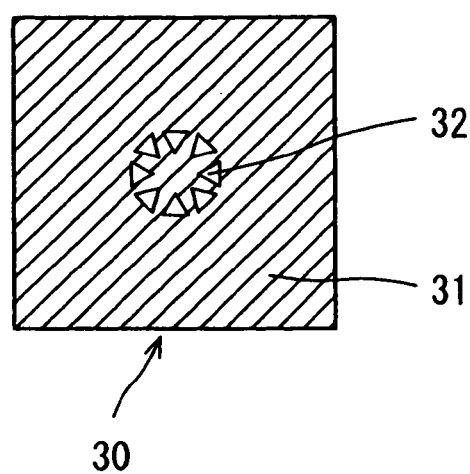
FIG. 4 is a plan view showing a structure of a mirror in a second variation according to the first embodiment of the present invention.

FIG. 4 is a plan view showing a structure of a mirror in a second variation according to the first embodiment of the present invention. In this second variation, the shape of a plurality of translucent portions in the first variation is varied. A mirror 30 in the second variation is constructed to have a reflecting film 31 similar to that in the first embodiment, and a light guiding portion 32 constructed by arranging a plurality of triangular translucent portions, which are formed to direct their vertical portions to a center, at an equal angle on the circle round the optical axis.

According to this structure, when the position of the eye is displaced from the optical axis, the user can understand simply in which direction the position of the eye should be moved, based on the direction of the sharp angle of the triangle and therefore the user can move quickly the position of the eye. Also, like the mirror 20 shown in FIG. 3, a loss of a quantity of light of the picked-up image can be reduced. In this case, eight triangular translucent portions constituting the light guiding portion 32 are illustrated in FIG. 4, but any number in excess of 2 may be employed. In the case where the number of the translucent portions arranged in the mirror 30 is reduced, such an arrangement may be employed that, for example, a plurality of translucent portions are positioned in the direction toward which the position of the eye is often displaced.

Figure 5:
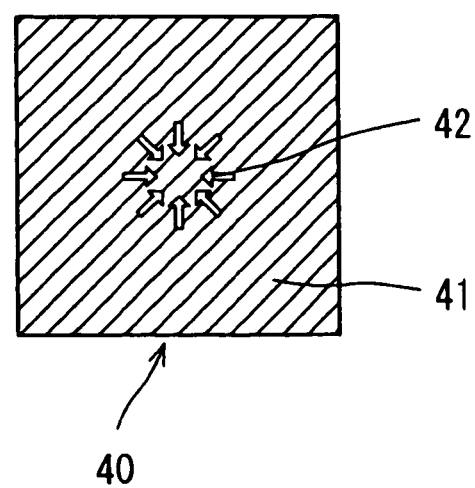
FIG. 5 is a plan view showing a structure of a mirror in a third variation according to the first embodiment of the present invention.

FIG. 5 is a plan view showing a structure of a mirror in a third variation according to the first embodiment of the present invention. In this third variation, the shape of a plurality of translucent portions in the first variation is varied. A mirror 40 in the third variation is constructed to have a reflecting film 41 similar to that in the first embodiment, and a light guiding portion 42 constructed by arranging a plurality of arrow-shaped translucent portions, which are formed to direct their pointed portions to a center, at an equal angle on the circle round the optical axis.

According to this structure, when the position of the eye is displaced from the optical axis, the direction toward which the position of the eye should be moved is pointed by the arrow and therefore the user can move simply and quickly the position of the eye based on the arrow. Also, like the mirror 20 shown in FIG. 3, a loss of a quantity of light of the picked-up image can be reduced. In this case, eight arrow-shaped translucent portions constituting the light guiding portion 42 are illustrated in FIG. 5, but any number in excess of 2 may be employed. In the case where the number of the translucent portions arranged in the mirror 40 is reduced, such an arrangement may be employed that, for example, a plurality of translucent portions are positioned in the direction toward which the position of the eye is often displaced.

(Second Embodiment)

Figure 6:
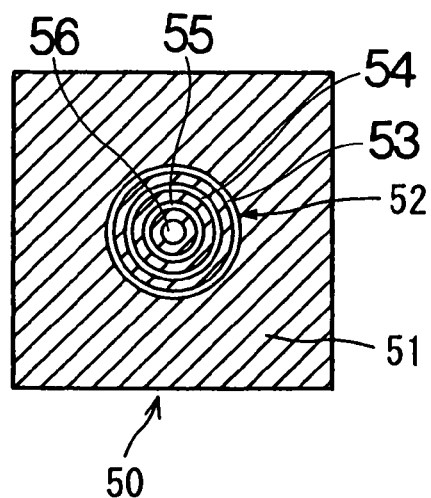
FIG. 6 is a plan view showing a structure of a mirror according to a second embodiment of the present invention.

A second embodiment shows another configurative example of the mirror and the light source. A basic structure of the eye image pick-up system according to the second embodiment is similar to that shown in FIG. 1(a), and structures of the mirror and the light source will be explained hereunder. FIG. 6 is a plan view showing a structure of a mirror according to the second embodiment of the present invention.

A mirror 50 in the second embodiment is constructed to have a reflecting film 51 formed by depositing the aluminum on the transparent substrate made of a plate-like glass or resin, and a transparent light guiding portion 52 having no deposition thereon. The light guiding portion 52 comprises three circular-ring translucent portions 53, 54, 55 arranged in a concentric fashion round the optical axis, and one circular translucent portion 56 a center of which is arranged on the optical axis.

Also, the light source for the guiding visible light corresponding to the LED 15 in FIG. 1(a) is constructed to have a plurality of LEDs arranged in such a way that at least adjacent translucent portions can emit the lights in different colors to respond to three circular-ring translucent portions 53, 54, 55 and one circular translucent portion in the light guiding portion 52 respectively. The lights are guided to respective translucent portions constituting the light guiding portion 52 by using the light guides. For example, in four translucent portions in total, the R light, the G light, the B light, and the R light are guided to the translucent portion 56, the translucent portion 55, the translucent portion 54, and the translucent portion 53 sequentially from the center respectively.

According to eye image pick-up system of the second embodiment, the guiding visible lights emitted from the LEDs can be seen in a wide range, and also a part of colors of the guiding visible lights being seen from the user at that position is changed when the position of the eye is displaced from the optical axis. Also, the colors of the guiding visible lights seen from the user at that position are changed according to an amount of positional displacement of the eye. In this manner, since the colors of the guiding visible lights seen from the user at that position are changed according to the direction in which the position of the eye is displaced from the optical axis or an amount of displacement, the user can recognize easily the position of the eye with respect to the optical axis and also a weak-sighted person can recognize simply the direction toward which the position of the eye should be moved. Therefore, the user can move quickly the position of the eye onto the optical axis even when the position of the eye is displaced.

In this case, in the above explanation, the light guiding portion 52 is constructed by three circular-ring translucent portions and one circular translucent portion, on which no deposition is formed. Any translucent portions may similarly implement the above light guiding portion if such translucent portions are a plurality of concentric translucent portions such as two circular-ring translucent portions or more, one circular-ring translucent portion or more and a circular translucent portion, or the like.

Figure 7:
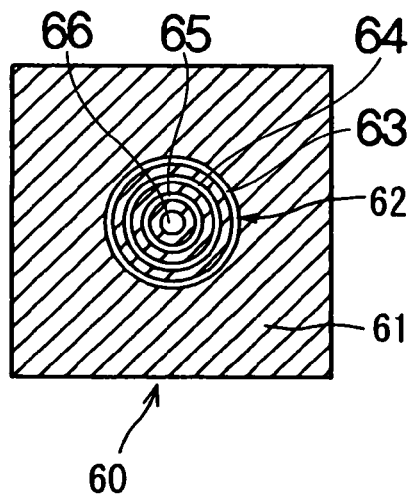
FIG. 7 is a plan view showing a structure of a mirror in a variation according to the second embodiment of the present invention.

Then, a variation of a mirror and a light source capable of achieving the similar advantages to the second embodiment will be explained with reference to FIG. 7 hereunder. FIG. 7 is a plan view showing a structure of a mirror in a variation according to the second embodiment of the present invention.

Like the second embodiment, a mirror 60 of this variation is constructed to have a reflecting film 61 formed by plating or depositing reflector material on the transparent substrate made of a resin, or the like, and a transparent light guiding portion 62. The light guiding portion 62 comprises three circular-ring translucent portions 63, 64, 65 arranged concentrically with the optical axis and one circular translucent portion 66 a center of which is arranged on the optical axis. At least adjacent translucent portions out of respective translucent portions are formed of colored translucent resins that are colored in different colors. For example, the translucent resins to transmit the R light, the G light, the B light, and the R light to the translucent portion 66, the translucent portion 65, the translucent portion 64, and the translucent portion 63 sequentially from the center respectively are provided in four translucent portions in total. Also, a white light source (not shown) is provided in place of the LED as the light source for the guiding visible light.

According to this configuration, like the second embodiment, a part of colors of the guiding visible lights being seen at that position is changed when the position of the eye is displaced from the optical axis. Also, the colors of the guiding visible lights seen from the user at that position are changed according to an amount of positional displacement of the eye. In this way, since the colors of the guiding visible lights seen from the user at that position are changed according to the direction in which the position of the eye is displaced from the optical axis or an amount of displacement, the user can recognize simply the direction toward which the position of the eye should be moved, based on the colors of the lights. Also, since only one white light source is needed as the light source, the light source can be constructed at a low cost. In this case, the circular-ring translucent portions constituting the light guiding portion 62 may be similarly implemented by any translucent portions if such translucent portions are a plurality of concentric translucent portions such as two circular-ring translucent portions or more, one circular-ring translucent portion or more and a circular translucent portion, or the like.

(Third Embodiment)

Figure 8:
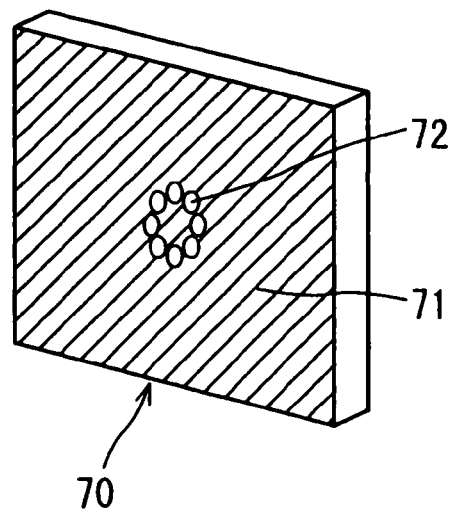
FIG. 8 is a plan view showing a structure of a mirror according to a third embodiment of the present invention.

A third embodiment shows other configurative example of a mirror. A basic structure of the eye image pick-up system according to the third embodiment is similar to that shown in FIG. 1(a), and a structure of the mirror will be explained hereunder. FIG. 8 is a plan view showing a structure of a mirror according to a third embodiment of the present invention.

A mirror 70 in the third embodiment is constructed to have a reflecting film 71 formed by plating or depositing reflector material on the transparent substrate made of a resin, or the like, and a light guiding portion 72 in which a plurality of circular openings are arranged concentrically with the optical axis like a circular ring. The light guiding portion 72 is formed by forming a plurality of circular openings as the translucent portions, which are arranged at an equal interval (equal angle) on the circle round the optical axis, by means of the integral molding. The opening portions are formed by providing the holes to pass the light through at least the reflecting surface on which the reflecting film 71 is formed, and have such a structure that the light passes through the mirror from a surface facing to the LED 15 to the reflecting surface. The guiding visible light from the LED 15 is passed through a plurality of openings of the light guiding portion 72, then is guided to the opposite side of the mirror 70, i.e., the side of the mirror 70 opposite to the LED 15, and then arrives at the eye 11 via the lens 13.

According to the eye image pick-up system of the third embodiment, like the above first embodiment, when the position of the eye is displaced from the optical axis, the user can recognize simply in which direction the position of the eye is displaced from the optical axis, according to how a part of circular-ring guiding visible light lacks. Also, since the light guiding portion 72 can be formed by the integral molding of the resin, such light guiding portion can be constructed at a low cost.

Figure 9:
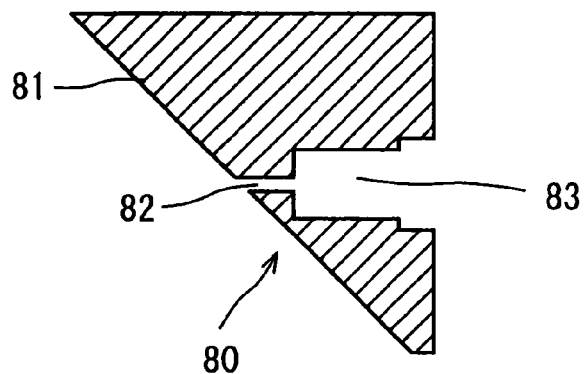
FIG. 9 is a sectional view showing a structure of a mirror in a variation according to the third embodiment of the present invention.

Then, other variation in which the light guiding portion is formed by the resin molding will be explained with reference to a sectional view in FIG. 9 hereunder. FIG. 9 is a sectional view showing a structure of a mirror in a variation according to the third embodiment of the present invention.

A mirror 80 in the variation is constructed to have a reflecting film 81 formed by plating or depositing reflecting material on the transparent substrate made of a resin, or the like, a light guiding portion 82 in which openings formed by a plurality of circular through holes are arranged concentrically with the optical axis like a circular ring, and an LED holding portion 83 provided to correspond to the light guiding portion 82. Although only one opening of the light guiding portion 82 is shown in a sectional view in FIG. 9, a plurality of circular through holes are formed as the translucent portions that are arranged at an equal interval (equal angle) on a circle round the optical axis. The light guiding portion 82 and the LED holding portion 83 are formed in the mirror 80 by the integral molding. The LED holding portion 83 is formed as the housing concave portion on the opposite side of the reflecting film 81 to communicate with the light guiding portion 82, and houses/holds the inserted LED as the light source therein.

According to this configuration, the mirror is formed inexpensively by the integral molding. Also, since the mirror is also used as the light-source holding portion, not only the number of articles can be reduced but also its assembling can be simplified and thus further reduction in a production cost can be achieved.

(Fourth Embodiment)

Figure 10:
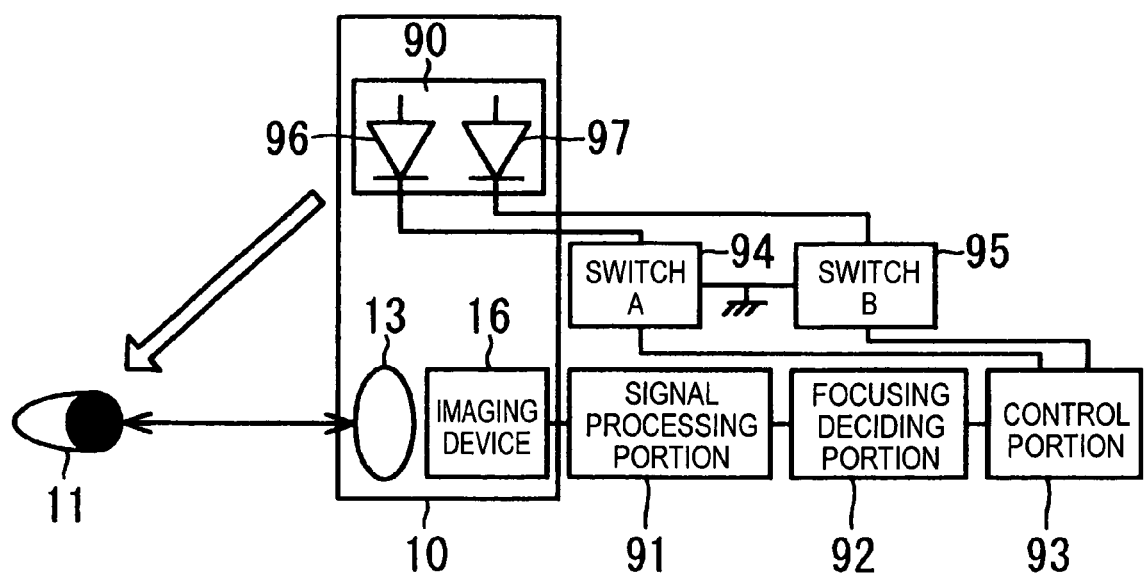
FIG. 10 is an explanatory view showing an eye image pick-up system and a configuration of the system according to a fourth embodiment of the present invention.

As described above, when the position of the eye coincides with the optical axis, the image of the eye can be picked up at the center. But the user must check whether or not the image is focused, by displaying the picked-up image on a monitor screen, or the like. A fourth embodiment shows a configuration of an eye image pick-up system that is capable of checking easily the focused condition of the eye image. FIG. 10 is an explanatory view showing an eye image pick-up system and a configuration of the system according to a fourth embodiment of the present invention.

The eye image pick-up system 10 in the fourth embodiment is constructed to have an LED portion 90 comprising a plurality (2 herein) of LEDs 96, 97 for emitting the visible lights in different colors respectively, in place of the LED 15 in the first embodiment. Also, the eye image pick-up system is constructed to have further a signal processing portion 91 for executing a signal processing of the eye image picked up by the eye image pick-up system 10, a focusing deciding portion 92 for deciding whether or not the eye image is focused, based on an image signal processed by the signal processing portion 91, a switch A 94 and a switch B 95 for controlling ON/OFF of the LEDs 96, 97 in the LED portion 90 respectively, and a control portion 93 for controlling ON/OFF of the switch A 94 and the switch B 95 based on the decision result in the focusing deciding portion 92.

The image signal of the eye image picked up by the imaging device 16 in the eye image pick-up system 10 and output therefrom is input into the signal processing portion 91 and is subjected to a predetermined video signal processing, then the focused condition of the eye image is decided by the focusing deciding portion 92 based on a high-frequency component, or the like in the image signal, and then the decision result is set out to the control portion 93. The control portion 93 controls ON/OFF of the switch A 94 and the switch B 95 in compliance with the decision result of the focused condition. At this time, the LEDs 96, 97 are caused to emit the lights in different colors at a duty ratio decided based on a degree to which the image is focused (focused degree) respectively by changing respective ON/OFF times of the switch A 94 and the switch B 95. For example, when the image is in the focused condition in which the image is focused properly, the duty ratio is controlled to prolong an ON time of the LED 96 per unit time and shorten an ON time of the LED 97. Then, the duty ratio is controlled to shorten an ON time of the LED 96 and prolong an ON time of the LED 97 as the image becomes out of focus. As a result, since a quantity of lights emitted from the LEDs 96, 97 in different colors respectively is changed, the color of the light emitted from the LED portion 90 is changed variously in response to the focused degree of the eye image.

According to the eye image pick-up system in the fourth embodiment, since the focused degree can be known from the change in the color of the light from the LED portion 90 in picking up the image of the eye, the user can be checked easily the focused position not to look at the picked-up image of the eye on the monitor screen, etc., and thus the user can move quickly the position of the eye to the focusing position. Also, if this system is combined with the light guiding portion in the first embodiment, the user can know a displacement of the position of the eye from the optical axis at the same time and thus the positioning of the optical axis and the focusing can be carried out easily. Therefore, the image of the eye can be picked up by moving quickly the position of the eye to the focused position on the optical axis.

Then, variations of the LED portion capable of achieving the similar advantages to the fourth embodiment will be explained with reference to the drawings hereunder.

Figure 11:
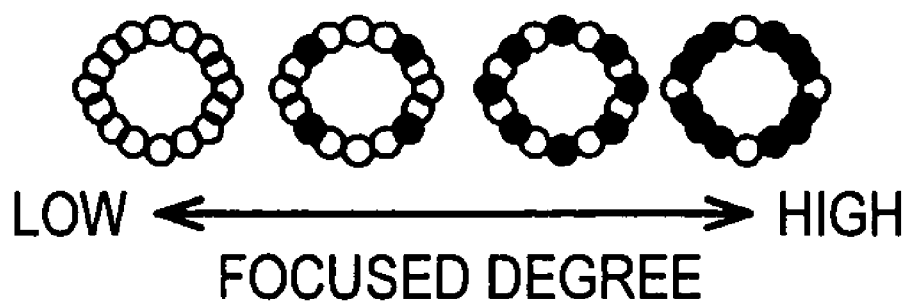
FIG. 11 is a plan view showing a configuration of an LED portion in a first variation according to the fourth embodiment of the present invention.

FIG. 11 is a plan view showing a configuration of an LED portion in a first variation according to the fourth embodiment of the present invention. In this first variation, the number of LEDs for emitting the light is changed according to the focused degree. An LED portion having a plurality of LEDs that are arranged to correspond to a plurality of circular-ring translucent portions of the light guiding portion 22 in the mirror 20 shown in FIG. 3 respectively is provided. Then, like the above fourth embodiment, the number of the LEDs that emit the light is changed in response to the focused degree by controlling ON/OFF of respective LEDs based on the focused degree. Here, as shown in FIG. 11, when the focused degree is high, the number of the LEDs that emit the light is reduced while, when the focused degree is low, the number of the LEDs that emit the light is increased gradually as the focused degree becomes lower.

According to this configuration, the user can decide readily the focused degree upon picking up the image by looking at the number of the LEDs that emit the guiding visible light, and thus the user can guide quickly the position of the eye to the focusing position.

FIG. 12 is a plan view showing a configuration of an LED portion in a second variation according to the fourth embodiment of the present invention. In this second variation, the psoitions of LEDs for emitting the light are changed according to the focused degree. An LED portion having a plurality of LEDs that are arranged to correspond to a plurality of circular-ring and circular translucent portions arranged concentrically in the light guiding portion 52 in the mirror 50 shown in FIG. 6 respectively is provided. Then, like the above fourth embodiment, the positions of the LEDs that emit the light are changed in response to the focused degree by controlling ON/OFF of respective LEDs based on the focused degree. Here, as shown in FIG. 12, when the focused degree is high, the LEDs corresponding to the circular translucent portion positioned at the center where the optical axis is positioned are caused to emit the light while, when the focused degree is low, the LEDs corresponding to the circular-ring translucent portions positioned on the outer peripheral side are caused gradually to emit the light as the focused degree becomes lower.

According to this configuration, the user can decide readily the focused degree upon picking up the image by looking at the positions of the LEDs that emit the guiding visible light, and thus the user can guide quickly the position of the eye to the focusing position.

(Fifth Embodiment)

In a fifth embodiment, a setting of a size of the light guiding portion in the eye image pick-up system will be explained concretely. FIG. 13 is an explanatory view showing an arrangement of constituent elements of an eye image pick-up system according to a fifth embodiment of the present invention. In this case, the same reference symbols are affixed to the same constituent elements as those in FIG. 1.

In the eye image pick-up system shown in FIG. 13, the front edge of the lens-barrel 12 has an iris function of the lens 13, wherein suppose that an aperture diameter of the lens-barrel 12 (iris) is A and a focal length of the lens 13 is f. Also, suppose that an image 19*a* of the light guiding portion 19 is projected to a position separated from the lens 13 by a distance Si to have a size di if a diameter of the light guiding portion 19 is set to d and a distance between the lens 13 and the light guiding portion 19 is set to s. In this case, the light guiding portion 19 is provided onto the mirror 14 to incline from the optical axis by about 45 degree, but such light guiding portion is illustrated perpendicular to the optical axis in FIG. 13, for convenience of explanation.

In this configuration, the size di of the image 19a of the light guiding portion 19 projected by the lens 13 is decided by the focal length f of the lens 13, the size d of the light guiding portion 19, and the distance s between the lens 13 and the light guiding portion 19, as given in following (Mathematical Expression 1).

$$d_i = \frac{s_i}{s}d = \frac{f \cdot d}{f - d} \quad \text{(Mathematical Expression 1)}$$

Therefore, the size di of the image 19a of the light guiding portion 19 viewed from the front surface of the lens 13 can be set arbitrarily based on (Mathematical Expressing 1), and the eye image pick-up system can be designed freely to meet to the applied device, Also, relationships between the position and the size of the user's eye as the subject and the light guiding portion will be explained hereunder. In FIG. 13, suppose that an interval between both eyes of the user is D and a distance (subject distance) from the front edge 12a of the lens-barrel to the eye 11 is L. At this time, an maximum angle α between the optical path of the image 19a of the light guiding portion, when viewed from the front edge 1a of the lens-barrel lens, and the optical axis and a glaring angle β formed when the user views the front edge 12a of the lens-barrel with one eye are derived by following (Mathematical Expressions 2).

$$\alpha = \tan^{-1}\left(\frac{\frac{t}{2} + \frac{d_i}{2}}{\frac{t}{2} + s_i}\right)$$

$$= \tan^{-1}\left(\frac{\frac{A}{2} + \frac{f \cdot s}{2(f-s)}}{\frac{t}{2} + \frac{f \cdot s}{f-s}}\right)$$

$$\beta = \tan^{-1}\left(\frac{\frac{D}{2} - \frac{A}{2}}{L}\right)$$

(Mathematical Expressions 2)

Here, in order to satisfy a relationship of α<β, the distance s between the lens 13 and the light guiding portion 19 and the size d of the light guiding portion 19 are set with respect to the aperture diameter A of the front edge 12a of the lens-barrel, the focal length f of the lens 13, and the subject distance L. In the case of α<β in (Mathematical Expressions 2), the user cannot look at the light guiding portion 18 simultaneously with both eyes. Accordingly, if respective values are set to satisfy this condition, the user is brought into such a condition that such user cannot look at the light guiding portion 18 with both eyes. As a result, since the position of the eye can be adjusted even though the user closes one eye (winks) or the user does not hide one eye, the position of the eye can be guided easily onto the optical axis.

(Sixth Embodiment)

Figure 14:
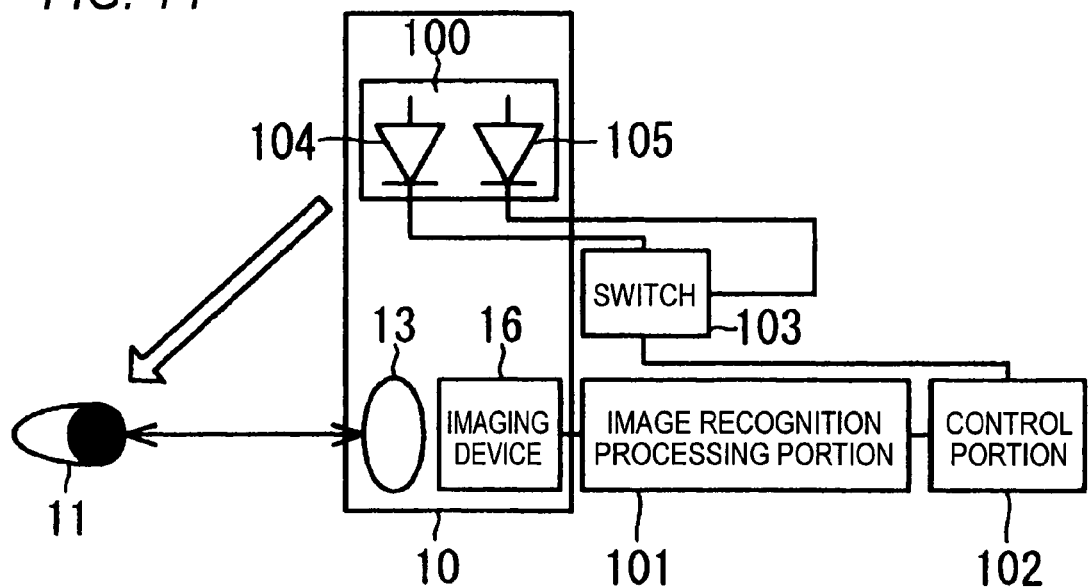
FIG. 14 is an explanatory view showing an eye image pick-up system and a configuration of the system according to a sixth embodiment of the present invention.
Figure 15:
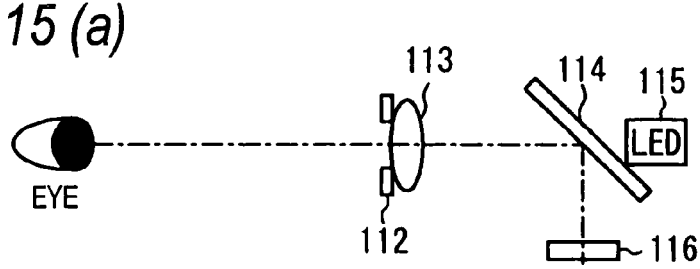
Figure 15:
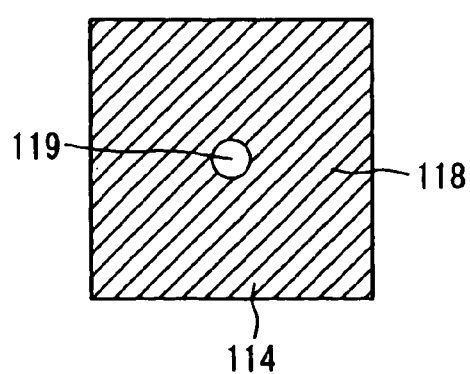
Figure 15:

FIG. 14 is an explanatory view showing an eye image pick-up system and a configuration of the system according to a sixth embodiment of the present invention.

An eye image pick-up system 10 is constructed to have an LED portion 100 having a plurality (2 herein) of LEDs 104, 105 that emit the visible light in different colors respectively, instead of the LED 15 in the first embodiment. Also, the eye image pick-up system is constructed to include an image recognition processing portion 101 for executing the image recognition process based on a signal of the eye image picked up by the eye image pick-up system 10, a switch 103 for controlling ON/OFF of the LEDs 104, 105 in the LED portion 100, and a control portion 102 for controlling ON/OFF of the switch 103 based on an output signal of the image recognition processing portion 101.

The image signal of the eye image picked up by the imaging device 16 of the eye image pick-up system 10 is input into the image recognition processing portion 101 and is subjected to the image recognizing process to decide which one of the right eye and the left eye was shot, according to a shape of an eyelid portion, or the like, and then the decision result is sent out to the control portion 102. The control portion 102 controls ON/OFF of the switch 103 based on the decision result of the eye image by the image recognition. At this time, the control portion 102 controls the switch 103 in such a way that the LED 104 in the LED portion 100 is turned ON when the eye that was shot was the left eye, while the LED 103 is turned ON when the eye that was shot was the right eye. As a result, the color of the guiding visible light emitted from the LED portion 100 is changed according to the eye that is going to be shot.

According to the eye image pick-up system in the sixth embodiment, in picking up the image of the eye, the user can know simply which eye of the right and left eyes is going to be put onto the optical axis, according to the color of the guiding visible light that the user can see via the light guiding portion. Therefore, the user can move quickly the position of the eye to a predetermined position.

According to the present embodiment mentioned above, since the circular-ring guiding visible light is employed, the user can find easily the guiding visible light to guide the position of the eye to be shot and also the user can know easily the direction toward which the position of the eye should be move. Therefore, the user can move quickly the position of the eye onto the optical axis.

Also, since a quantity of generated light, the light emitting position, the color, or the like of the guiding visible light is changed based on the focused degree of the picked-up image of the eye are changed, the user can decide easily in which direction the position of the eye to be shot should be moved back and forth with respect to the focusing position. Also, since the color, or the like of the guiding visible light is changed based on the image recognition of the images of the left and right eyes that were shot, the user can discriminate easily which one of the right and left eyes is going to be shot. In addition, since the present embodiment can attain the above advantages not to employ the complicated configuration, the eye position guiding device can be constructed at a low cost.

The present invention is explained in detail with reference to particular embodiments. But it is apparent for the person skilled in the art that various variations and modifications may be applied without departing a spirit and a scope of the present invention.

This application is filed based on Japanese Patent Application (Patent Application No. 2002-096057) filed on Mar. 29, 2002 and the contents thereof are incorporated herein by the reference.

INDUSTRIAL APPLICABILITY

As described above, according to the present invention, in the eye image pick-up system that has the eye position guiding device for guiding the position of the eye to be shot when the user looks at the visible-light light source provided onto the optical axis of the imaging optical system through the light guiding means, the user as a subject can find easily out the guiding visible light and guide quickly the position of the eye onto the optical axis. Therefore, the user can guide quickly the position of the eye onto the optical axis.

The invention claimed is:

1. An eye image pick-up system for picking up an image of an eye by using an objective lens and an imaging device, said system comprising:
    a mirror portion provided between the objective lens and the imaging device, for turning an optical path of an optical system;
    a light source provided at a back of the mirror portion on a prolonged line of the optical axis that extends from the objective lens to the mirror portion in the optical path, for emitting a visible light; and
    a light guiding means provided to the mirror portion, for guiding the visible light from the light source to an objective lens side;
    wherein the light guiding means is constructed by translucent members that are provided concentrically round the optical axis.

2. The eye image pick-up system according to claim 1, wherein the light guiding means has a circular-ring translucent portion formed round the optical axis on a reflecting surface of the mirror portion.

3. The eye image pick-up system according to claim 1, wherein the light guiding means has a plurality of translucent portions formed on a reflecting surface of the mirror portion and arranged on a circle round the optical axis.

4. The eye image pick-up system according to claim 3, wherein the plurality of translucent portions of the light guiding means are formed of a plurality of triangular translucent portions that are aligned at an equal angle on a circle round the optical axis to direct respective sharp angles to the optical axis.

5. The eye image pick-up system according to claim 3, wherein the plurality of translucent portions of the light guiding means are formed of a plurality of arrow-shaped translucent portions that are aligned at an equal angle on a circle round the optical axis to direct respective pointed portions to the optical axis.

6. The eye image pick-up system according to any one of claims 1 to 5,
    wherein the light guiding means has translucent portions formed of openings that are formed on a reflecting surface of the mirror portion.

7. The eye image pick-up system according to claim 3, wherein the light guiding means has a plurality of circular-ring or circular translucent portions that are formed concentrically round the optical axis on a reflecting surface of the mirror portion, and
    wherein the light source has a plurality of light sources at least adjacent light sources of which emit lights in different colors to the plurality of translucent portions.

8. The eye image pick-up system according to claim 1,
    wherein the light guiding means has a plurality of circular-ring or circular translucent portions that are formed concentrically round the optical axis on a reflecting surface of the mirror portion,
    wherein the translucent portions are formed of colored translucent portions at least adjacent translucent portions of which pass through lights in different colors, and
    wherein the light source has a white light source that emits a light to the plurality of translucent portions.

9. The eye image pick-up system according to claim 1,
    wherein the mirror portion is molded with resin material on one surface of which a reflecting surface is formed, and
    wherein the light guiding means has a plurality of translucent portions formed of openings that are aligned on a circle round the optical axis on a reflecting surface of the mirror portion.

10. The eye image pick-up system according to any one of claims 1, 2, 3 and 9
    wherein the light source has a plurality of color light sources that emit a light in different colors respectively, and
    said system further comprising:
    a focusing deciding means for deciding a focused condition of the image of the eye picked up by the imaging device; and
    a light emission controlling means for controlling light emitting times of the light sources in respective colors based on a decision result of the focused condition.

11. The eye image pick-up system according to claim 3 or claim 9, further comprising:
    a focusing deciding means for deciding a focused condition of the image of the eye picked up by the imaging device; and
    a light emission controlling means for changing a number of lights that pass through the plurality of translucent portions of the light guiding means, in response to a decision result of the focused condition.

12. An eye image pick-up system according to claim 3 or claim 9, further comprising:
    a focusing deciding means for deciding a focused condition of the image of the eye picked up by the imaging device; and
    a light emission controlling means for changing positions of lights that pass through the plurality of translucent portions of the light guiding means, in response to a decision result of the focused condition.

13. The eye image pick-up system according to any one of claims 1, 2, 3 and 9
    wherein the light source the light source has a plurality of color light sources that emit a light in different colors respectively, and
    said system further comprising:
    an image discriminating means for discriminating to which one of right and left eyes the eye the image of which is picked up by the by the imaging device corresponds; and
    a light emission controlling means for changing a color of a light emitted from the light source in response to a decision result of the focused condition.

14. The eye image pick-up system according to claim 1,
    wherein the mirror portion has a holding portion that is provided to communicate with the openings and holds the light source.

* * * * *